US006785357B2

(12) United States Patent
Bernardi et al.

(10) Patent No.: US 6,785,357 B2
(45) Date of Patent: Aug. 31, 2004

(54) HIGH ENERGY X-RAY MOBILE CARGO INSPECTION SYSTEM WITH PENUMBRA COLLIMATOR

(75) Inventors: Richard T. Bernardi, Prospect Heights, IL (US); John F. Moore, Libertyville, IL (US)

(73) Assignee: Bio-Imaging Research, Inc., Lincolnshire, IL (US)

( * ) Notice: Subject to any disclaimer, the term of this patent is extended or adjusted under 35 U.S.C. 154(b) by 35 days.

(21) Appl. No.: 10/346,143

(22) Filed: Jan. 16, 2003

(65) Prior Publication Data

US 2004/0141584 A1 Jul. 22, 2004

(51) Int. Cl.[7] ............................................. G01N 23/04
(52) U.S. Cl. ........................ 378/57; 378/193; 378/196
(58) Field of Search ..................... 378/57, 193, 196, 378/62, 147, 98.8

(56) References Cited

U.S. PATENT DOCUMENTS

| 5,638,420 A | 6/1997 | Armistead |
| 5,692,028 A | 11/1997 | Geus et al. |
| 5,764,683 A | 6/1998 | Swift et al. |
| 6,058,158 A | 5/2000 | Eiler |
| 6,292,533 B1 * | 9/2001 | Swift et al. .................. 378/57 |
| 6,636,581 B2 * | 10/2003 | Sorenson .................... 378/58 |
| 2001/0021241 A1 | 9/2001 | Swift et al. |
| 2002/0136353 A1 | 9/2002 | Kang et al. |
| 2004/0017887 A1 * | 1/2004 | Le et al. ..................... 378/57 |

* cited by examiner

Primary Examiner—Craig E. Church
Assistant Examiner—Irakli Kiknadze
(74) Attorney, Agent, or Firm—Welsh & Katz, Ltd.

(57) ABSTRACT

A non-invasive method and apparatus are described for inspecting a cargo container. The method includes the steps of disposing an X-ray source and an X-ray detector on opposing ends of a rotatable boom, rotating the boom in a horizontal plane so that the X-ray source and X-ray detector straddle the cargo container and providing translational relative movement between the boom and cargo container while the X-ray source irradiates the container and the X-ray detector detects and measures X-ray energy passing through the container from the X-ray source.

30 Claims, 2 Drawing Sheets

HIGH ENERGY X-RAY MOBILE CARGO INSPECTION SYSTEM WITH PENUMBRA COLLIMATOR

FIELD OF THE INVENTION

The field of the invention relates to X-ray imaging systems and more particularly to cargo inspections systems.

BACKGROUND OF THE INVENTION

Portable X-ray inspection systems for trucks are generally known. Such systems are typically used to perform non-invasive inspection of trucks for contraband (e.g., explosives, drugs, etc.). Often an X-ray beam is directed through the truck to a set of detectors on an opposing side.

As the radiation of the X-ray beam passes through the truck, the contents of the truck attenuate the beam based upon the density of the contents. Based upon the attenuation, an image may be formed of the truck's contents. By comparing a truck's manifest with the X-ray image, law-enforcement personnel may make a determination of whether on not they have probable cause to believe that any laws have been broken.

One form of such devices is constructed in the form of a gantry with an X-ray source on one side and an X-ray detector on an opposing side. A hoist is usually provided to raise and lower the X-ray source or detector in unison. Such devices may be rubber tire or rail mounted.

In order for the gantry to span a semi-tractor trailer, the gantry must necessarily be quite high and quite wide (e.g., four or more feet higher and wider than the semi-tractor trailer). Because of the height and width of gantry-type inspection systems, they are generally not regarded as being very mobile and generally require special permits for highway travel.

Other truck inspection devices have used X-ray sources mounted to a truck-bed and a moveable boom to position a detector on an opposing side of the truck to be inspected. When not in use, the moveable boom could be folded and stored in a position directly above a centerline of the truck.

Because of the relatively stationary location of the X-ray source on the truck bed, such systems have difficulty effectively inspecting locations on trucks that are close to the road or on the top of the truck adjacent the X-ray source. As a result, the X-ray detectors are often exceptionally large to cover peripheral areas which adds to the overall size and expense of such systems. In addition, because of the difficulty in scanning peripheral areas, such systems are not readily adaptable to a variety of different cargo-handling enclosures.

While existing portable X-ray inspection systems have been effective, their size has impeded their use. Because of the importance of cargo inspection, a need exists for a X-ray inspection system that is mobile and adaptable to a variety of applications.

SUMMARY

A non-invasive method and apparatus are described for inspecting a cargo container. The method includes the steps of disposing an X-ray source and an X-ray detector on opposing ends of a rotatable boom, rotating the boom in a horizontal plane so that the-X-ray source and X-ray detector straddle the cargo container and providing translational relative movement between the boom and cargo container while the X-ray source irradiates the container and the X-ray detector detects and measures X-ray energy passing through the container from the X-ray source.

DETAILED DESCRIPTION OF AN ILLUSTRATED EMBODIMENT

Figure 1:
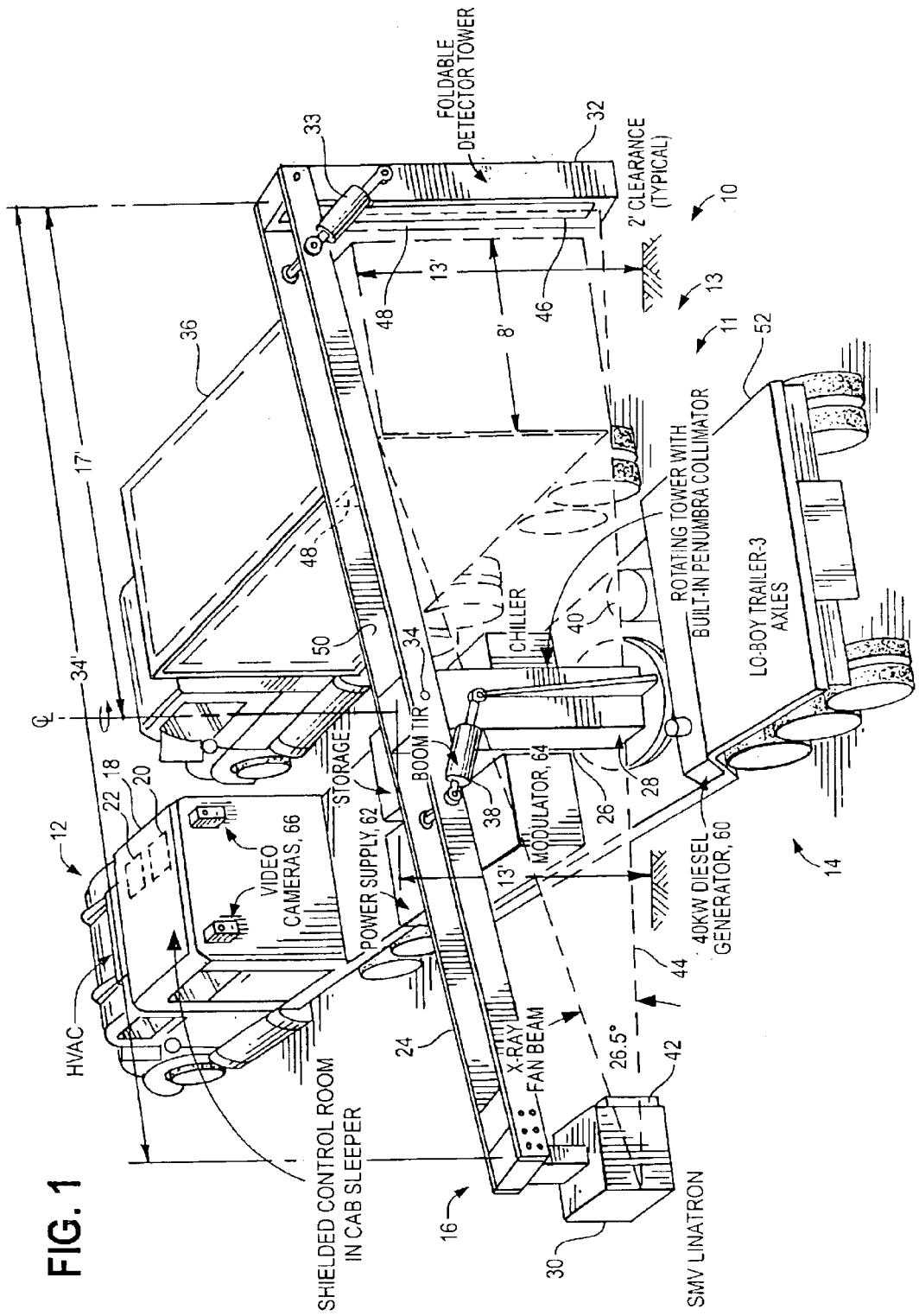
FIG. 1 is a rear perspective view of a mobile cargo inspection system in accordance with an illustrated embodiment of the invention.

FIG. 1 is a rear perspective view of a mobile X-ray inspection system 10, shown in a context of use generally in accordance with an illustrated embodiment of the invention. The system-10 may include a truck (e.g., a semi-tractor 12 and a lo-boy trailer 14). Mounted within a cab 18 of the semi-tractor 12 and to the trailer 14 is a self-contained X-ray imaging system 11. An image processor 20 and display 22 of the system 11 may be mounted within the cab 18 and image-gathering hardware may be mounted to a bed of the trailer 14.

An X-ray source 30 and an X-ray detector tower 32 may form counterbalancing elements on opposing ends of a rotatable and tiltable boom 24. While the X-ray source 30 and detector 32 are shown as being equally spaced from a center point defined by a center pin 34 of the boom 24, the spacing on each side of the center point may also be made inversely proportional to the respective weights of the source 30 and detector tower 32 so that the detector tower 32 substantially balances the weight of the source 30.

The detector tower 32 is turn may be located directly above a longitudinal centerline of the truck. The balancing of the boom 24 above the longitudinal centerline of the truck is considered to be particularly advantageous because it allows the system 11 to be used without outriggers or fear of the truck overturning.

The boom 24, in turn, may be supported by a rotatable tower (support post) 26. The rotatable support post 26 may be coupled to the trailer 14 through use of an annular bearing and locking collar (not shown). A rotational actuator (e.g., an electric motor) 40 may be provided to rotate the support post 26.

The center pin 34 may pass through a set of holes in the boom 24 and post 26 thereby providing a pivot point that allows the boom 24 to tilt as necessary to clear a cargo container (e.g., a semi-tractor trailer) 36. An actuator (e.g., a hydraulic cylinder) 38 may be provided to control the tilt of the boom 24 as necessary to the application.

The X-ray source 30 may be any appropriate high-energy X-ray source (e.g., a.6 MV Linatron). A first and second collimator 28, 42 may be used to precisely focus the X-ray beam 44 on a linear set of detectors 46 on the detector tower 32. The focusing of the X-ray beam 44 on the detectors 46 is important not only for safety, but also to ensure that predefined levels of X-ray energy pass through the cargo container 36. The use of the predefined levels of X-ray energy allows the contents of the cargo container 36 to be identified with a great deal of certainty based upon the absorption rates of predetermined categories of contraband (e.g., heroin, explosives, etc.).

The first collimator 42 may be conventional. An aperture of the first collimator 42 may be structured to create a fan-beam shaped X-ray envelope that diverges at an appropriate fan angle (e.g., 26.5 degrees) in a vertical direction. The vertical size of the collimator 42 may be chosen to allow the X-ray beam 44 to span an appropriate interrogation height (e.g., 11 feet) of a cargo container 36 located between the center pin 34 and detectors 32.

The horizontal size of the collimator 42 may be relatively small. The small size (e.g., in the millimeter or submillimeter range) allows a relatively small longitudinal distance on the cargo container 36 to interrogated at a time.

The second collimator 28 may be fabricated into the structure of the rotating tower 26. The second collimator 28 functions to return a sharp edge to the X-ray beam 44 and to further reduce the possibility of-X-ray leakage into the environment.

Figure 2:
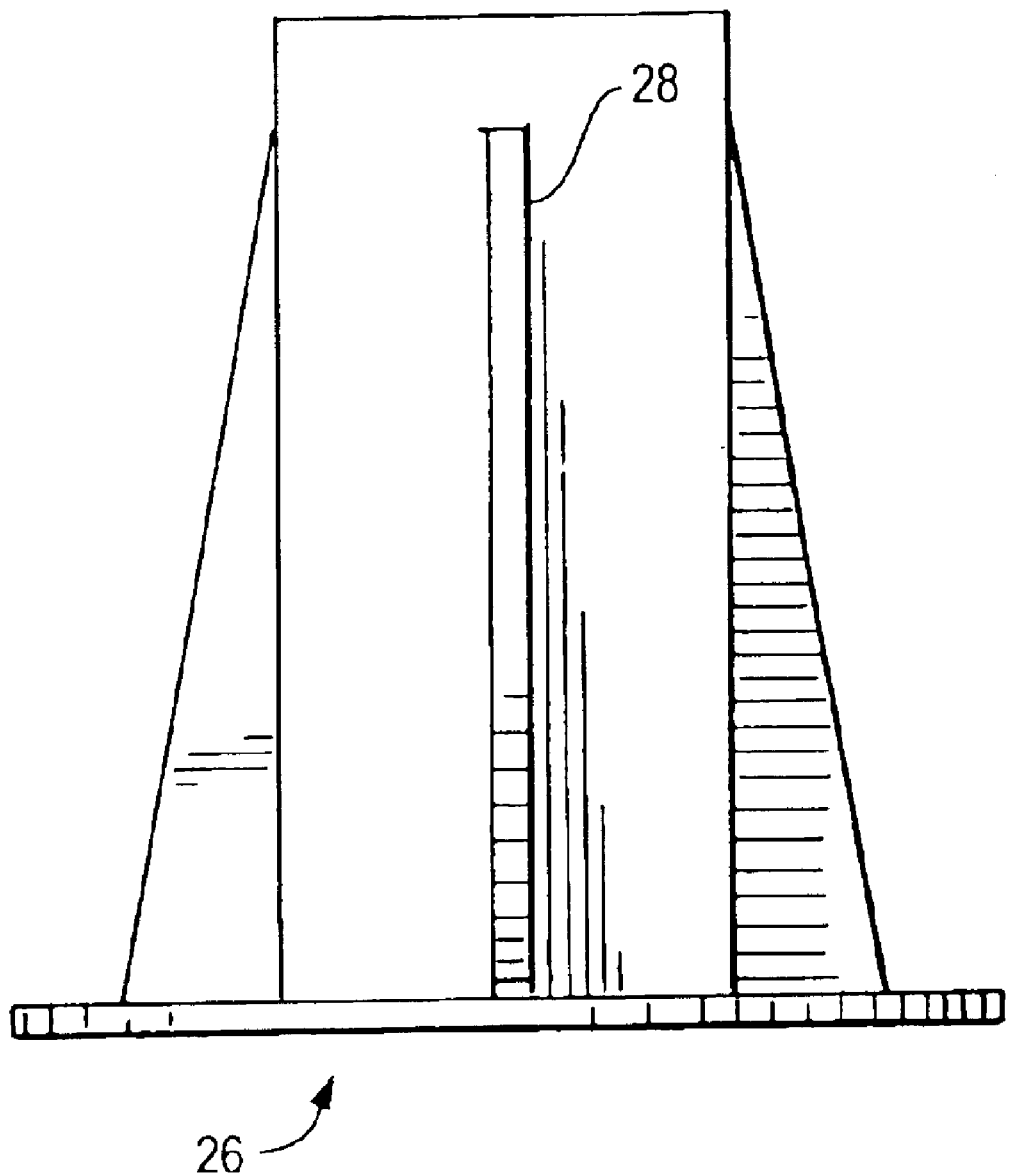
FIG. 2 is a rotating tower that may be used with the system of FIG. 1.

FIG. 2 depicts a side view of the tower 26. As may be seen in the side view, the second collimator 28 has the form of a vertical slot in the tower 26.

The detectors 46 may consist of a vertical linear array of 6 MV X-ray detector elements with a pitch (center to center distance) of approximately 1.38 mm for receiving the vertical fan beam 44 of X-rays. One or more vertical columns of detectors may be used (either aligned horizontally or offset by one-half the pitch) to improve resolution. A guard band 48 of X-ray absorbing material may be provided around the detectors 46 to absorb excess X-rays. The operation of the detectors 46 in conjunction with the processor 22 and display 20 provides a digital radiographic image of the contents of the cargo container 36.

It should be noted that the aperture size of the first and second collimators 28, 42 are proportioned based upon the distance separating the X-ray generator within the X-ray source 30 and the vertical array of detectors 46. For example the ratio between the height of the X-ray detectors 46 and the distance to the X-ray generator is the same ratio that exists between the height of the vertical aperture in the second collimator 28 and the distance to the X-ray generator and also the same ratio between the height of the vertical aperture in the first collimator 42 and the distance to the X-ray generator. The same relationship also exists in the ratio between the width of the X-ray detectors 46 and the distance to the X-ray generator and the ratio between the width of the horizontal apertures in the first and second collimator 28, 42 and respective distances to the X-ray generator.

It should also be noted that where a centerline of the X-ray beam 44 is oriented to be parallel with the length of the boom 24 (when viewed from above), the X-ray beam 44 is automatically aligned with the second collimator 28 and detector tower 32. By building the second collimator 28 into the tower 26 and allowing it to rotate with the boom 24, the second collimator 28 is automatically aligned with the X-ray source 30 and detectors 46 no matter what angle the boom 24 assumes.

When not in use, the detector tower 32 may be folded by an actuator (e.g., a hydraulic cylinder) 33 into the slot 50 at the end of the boom 24 as shown by dotted line 48. The boom 24 may then be rotated counterclockwise to a position parallel to the longitudinal axis of the tractor 12 and trailer 14 combination for transport. With the boom 24 in the transport position, the folded detector boom 32 would lie directly over the tractor 12 and the source 30 would lie over a rear deck 52 of the trailer 14.

In order to power the inspection system 10, a self-contained power source (e.g., a diesel generator) 60 may be located on the trailer 14 rearward of the tower 26. A high voltage power supply 62 and modulator 64 may be driven by the power source 60 to excite the X-ray source. Similarly, the processor 20 and display may be powered by the self-contained power source 60.

A pair of video cameras 66 may be provided to allow an operator inside the cab 18 to operate the boom 24 without leaving the cab 18. The video cameras 66 may be coupled to the display 22 to further reduce the space that separate monitors would otherwise require.

In operation, the system 10 may be driven to virtually any remote location and the boom 24 rotated to define an inspection space 13 between the trailer 14 and detector tower 32. Images of the contents of the cargo container 36 may be obtained by effecting relative movement between the trailer 14 and cargo container 36 by means of an actuator. Relative movement may be accomplished by using the tractor 12 as an actuator to pull the trailer 14 past the cargo container 36 or by using a tractor of the container 36 as an actuator to drive the cargo container 36 through the inspection space 13.

The system 10 offers a number of advantages over the prior art. One of the greatest advantages over gantry-style or other type inspection systems is the mobility of the system 10. The truck mounted imaging system 11 allows the cargo inspection system 10 to be taken almost anywhere. The on-board power source allows the system 10 to operate in areas without the infrastructure needed by other systems.

The use of the boom 24 and counterbalancing X-ray source and detectors maintains a center of gravity of the system 11 over the centerline of the truck. Maintaining the center of gravity over the truck allows for the use of the imaging system 11 without outriggers or other special support structure.

The use of the boom 24 also allows for greater imaging flexibility. For example, in the case of smaller vehicles (and to a lesser extend with larger vehicles), the boom 24 may be tilted up or down (or from side to side) to move the interrogation zone 13 up or down (or side to side) as appropriate to the situation. The movement of the boom 24, during relative motion between the imaging system 11 and cargo container 36 also allows for the possibility of binocular imaging of the cargo container 36.

A specific embodiment of a method and mobil apparatus for inspecting cargo according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention, any and all modifications, variations, or equivalents that fall within the true spirit basic underlying principles disclosed and claimed herein.

What is claimed is:

1. A non-invasive method for inspecting a cargo container, such method comprising the steps of:
   disposing an X-ray source and an X-ray detector on opposing ends of a rotatable boom;
   rotating the boom in a horizontal plane so that the X-ray source and X-ray detector straddle the cargo container; and
   providing translational relative movement between the boom and cargo container while the X-ray source irradiates the container and the X-ray detector detects and measures X-ray energy passing through the container from the X-ray source.

2. The non-invasive method as in claim 1 wherein the rotatable boom further comprises a trailer supporting the rotatable boom.

3. The non-invasive method as in claim 2 wherein the trailer further comprises a flat-bed semi-tractor trailer.

4. The non-invasive method as in claim 2 wherein the rotatable boom supported by the trailer further comprises a support post secured to the trailer at a first end and to a center portion of the boom on a second, opposing end.

5. The non-invasive method as in claim 4 further comprising collimating an X-ray beam from the X-ray source within a collimator disposed in the support post.

6. The non-invasive method as in claim 1 wherein the cargo container further comprises a semi-tractor trailer.

7. The non-invasive method as in claim 1 further comprising tilting the boom to clear the cargo container.

8. The non-invasive method as in claim 1 further comprising folding the X-ray detector into the boom for transport.

9. The non-invasive method as in claim 1 further comprising proportioning the boom so that the X-ray source substantially counterbalances the X-ray detector.

10. The non-invasive method as in claim 1 further comprising processing the detected X-rays to form a two-dimensiona image of the cargo container.

11. The non-invasive method as in claim 1 further comprising processing the detected X-rays to form a binocular image of the cargo container.

12. An apparatus for performing non-invasive inspection of a cargo container, such apparatus comprising:
means for supporting an X-ray source and an X-ray detector on opposing sides of an inspection area;
rotating the means for supporting in a horizontal plane so that the X-ray source and X-ray detector straddle the cargo container located within the inspection area; and
means for providing translational relative movement between the means for supporting and cargo container while the X-ray source irradiates the container and the X-ray detector detects and measures X-ray energy passing through the container from the X-ray source.

13. The apparatus for performing non-invasive inspection as in claim 12 wherein the rotatable means for supporting further comprises a trailer.

14. The apparatus for performing non-invasive inspection as in claim 13 wherein the trailer further comprises a flat-bed semi-tractor trailer.

15. The apparatus for performing non-invasive inspection as in claim 12 wherein the cargo container further comprises a semi-tractor trailer.

16. The non-invasive method as in claim 15 further comprising means for collimating an X-ray beam from the X-ray source disposed within the means for supporting.

17. The apparatus for performing non-invasive inspection as in claim 12 further comprising means for tilting the means for supporting to clear the cargo container.

18. The apparatus for performing non-invasive inspection as in claim 12 further comprising means for folding the X-ray detector into the means for supporting for transport.

19. An apparatus for non-invasively inspecting a cargo container, such apparatus comprising:
a rotatable boom;
an X-ray source and an X-ray detector on opposing ends of the rotatable boom;
an actuator adapted to rotate the boom in a horizontal plane so that the X-ray source and X-ray detector straddle the cargo container; and
an actuator adapted to provide translational relative movement between the boom and cargo container while the X-ray source irradiates the container and the X-ray detector detects and measures X-ray energy passing through the container from the X-ray source.

20. The apparatus for non-invasively inspecting a cargo container as in claim 19 wherein the rotatable boom further comprises a trailer supporting the rotatable boom.

21. The apparatus for non-invasively inspecting a cargo container as in claim 20 wherein the trailer further comprises a flat-bed semi-tractor trailer.

22. The apparatus for non-invasively inspecting a cargo container as in claim 20 wherein the rotatable boom supported by the trailer further comprises a support post secured to the trailer at a first end and to a center portion of the boom on a second, opposing end.

23. The apparatus for non-invasively inspecting a cargo container as in claim 22 further comprising a collimator disposed in the support post.

24. The apparatus for non-invasively inspecting a cargo container as in claim 19 wherein the cargo container further comprises a semi-tractor trailer.

25. The apparatus for non-invasively inspecting a cargo container as in claim 19 further comprising an actuator adapted to tilt the boom to clear the cargo container.

26. The apparatus for non-invasively inspecting a cargo container as in claim 19 further comprising a processor adapted to process the detected X-rays to form an X-ray image of the cargo container.

27. An apparatus for non-invasively inspecting a cargo container, such apparatus comprising:
a truck;
rotatable boom;
an X-ray source and an X-ray detector disposed on opposing ends of the rotatable boom;
a rotating tower for supporting the rotatable boom secured to the truck on a first end and the rotatable boom on a second end; and
a collimator disposed within the support post.

28. The apparatus for non-invasively inspecting a cargo container as in claim 27 further comprising an actuator adapted to rotate the boom in a horizontal plane so that the X-ray source and X-ray detector straddle the cargo container.

29. The apparatus for non-invasively inspecting a cargo container as in claim 27 further comprising an actuator adapted to provide translational relative movement between the boom and cargo container while the X-ray source irradiates the container and the X-ray detector detects and measures X-ray energy passing through the container from the X-ray source.

30. A mobile cargo inspection apparatus comprising:
a trailer;
a support post extending upwards from the trailer;
a boom disposed across an upper end of the post;
an X-ray source disposed on a first end of the boom; and
an X-ray detector array disposed on a second, opposing end of the boom, said boom being arranged to rotate to a position transverse to a longitudinal axis of the trailer so as to create an X-ray interrogation space for cargo inspection between the X-ray detector and side of the trailer.

* * * * *